(12) United States Patent
Bechtold et al.

(10) Patent No.: US 6,641,560 B1
(45) Date of Patent: Nov. 4, 2003

(54) INJECTING DEVICE

(75) Inventors: Herbert Bechtold, Villingen-Schwennigen (DE); Jochen Gabriel, Stuttgart (DE)

(73) Assignee: B. D. Medico S.a.r.l., Mies (CH)

( * ) Notice: Subject to any disclaimer, the term of this patent is extended or adjusted under 35 U.S.C. 154(b) by 0 days.

(21) Appl. No.: 09/857,717

(22) PCT Filed: Dec. 10, 1999

(86) PCT No.: PCT/EP99/09765

§ 371 (c)(1),
(2), (4) Date: Jun. 8, 2001

(87) PCT Pub. No.: WO00/35516

PCT Pub. Date: Jun. 22, 2000

(30) Foreign Application Priority Data

Dec. 17, 1998 (DE) .................................. 298 22 494 U

(51) Int. Cl.⁷ .............................................. A61M 5/20
(52) U.S. Cl. ....................................... 604/136; 604/157
(58) Field of Search ................................. 604/130, 134, 604/136, 137, 138, 139, 156, 157, 187, 192, 199, 232, 234

(56) References Cited

U.S. PATENT DOCUMENTS

| 5,042,977 A | 8/1991 | Bechtold et al. ............ 604/134 |
| 5,114,406 A | 5/1992 | Gabriel et al. ............... 604/136 |
| 5,320,609 A * | 6/1994 | Haber et al. ................. 604/135 |
| 5,358,489 A | 10/1994 | Wyrick ........................ 604/136 |
| 5,478,316 A | 12/1995 | Bitdinger et al. ........... 604/135 |
| 5,480,387 A | 1/1996 | Gabriel et al. ............... 604/134 |
| 5,514,097 A | 5/1996 | Knauer ........................ 604/136 |
| 5,540,664 A | 7/1996 | Wyrick ........................ 604/136 |
| 5,665,071 A | 9/1997 | Wyrick ........................ 604/134 |
| 5,695,472 A | 12/1997 | Wyrick ........................ 604/136 |
| 5,709,662 A | 1/1998 | Olive et al. ................. 604/135 |
| 5,833,669 A | 11/1998 | Wyrick ........................ 604/234 |
| 6,241,709 B1 | 6/2001 | Bechtold et al. ............ 604/207 |

FOREIGN PATENT DOCUMENTS

| EP | 0 525 525 | 2/1993 | ............ A61M/5/20 |
| EP | 0 666 084 | 8/1995 | ............ A61M/5/20 |

* cited by examiner

Primary Examiner—Brian L. Casler
Assistant Examiner—Catherine Serke
(74) Attorney, Agent, or Firm—Milton Oliver; Ware, Fressola, VDS & Adolphson

(57) ABSTRACT

An injection device has a housing (12) in which a container (14) for receiving an injectable fluid (18) is longitudinally movable. To its proximal end, an injection needle (26) can be releasably coupled. The injection device has a spring (50) associated with a releasable detent (52) for latching this spring (50) in a cocked configuration (FIG. 2). Further, there is a cocking member (40) insertable into the proximal end of the housing (12) for moving the longitudinally movable container (14) in the distal direction and for thereby bringing the spring (50) into the cocked configuration.

1 Claim, 3 Drawing Sheets

INJECTING DEVICE

REFERENCE TO RELATED APPLICATION

This application is a §371 of PCT/EP99/09765 filed DEC. 10, 1999.

1. Field of the Invention

The invention relates to an injecting device having a housing, in which a container of injectable fluid is arranged in a longitudinally movable manner, the container being adapted for releasably attaching, at its proximal end, an injection needle.

2. Background

In connection with injecting devices, it is a problem, especially for older patients, prior to an injection, to place these devices in a particular position, in which, for example, the dose can be set or from which the carrying out of an injection is possible.

SUMMARY OF THE INVENTION

It is therefore an object of the invention to provide a new injecting device.

In accordance with the invention, this object is achieved by an injecting device having a housing, in which a container for receiving an injectable fluid is arranged in a longitudinally movable manner, on which container an injection needle can be releasably mounted at the proximal end, having a spring which is associated with a releasable detent, in order to latch this spring in a compressed configuration, and having a cocking member, which can be inserted into the proximal end of the housing in order to shift the longitudinally movable container in the distal direction and thereby to put the spring into a compressed configuration. By using a cocking member, which is inserted into the proximal end of the housing, and thereby shifts the container into a cocked configuration, one obtains a simple actuation. At the same time, the cocking member can serve as a cover cap, in order to protect the mechanism of the injection device against contamination.

Injection devices having hidden needles do not permit the patient to readily see whether or not an injection needle is mounted. This needle is usually swapped out after an injection, but if the patient forgets, after unscrewing the old needle, to screw on a new one, it can happen that he tries an "injection" without a needle, which of course means nothing is injected.

Therefore, according to a further feature of the invention, the contact between the cocking member and the container is so formed that the spring can be latched into the compressed configuration if a needle is mounted, but cannot be if no needle is mounted. One thus achieves that, without a needle, the spring cannot be latched into the compressed configuration, so that a subsequent triggering of an injection by release of the detent is not possible. Thereby, the patient is effectively reminded that he must put in place a new needle, since without it, he cannot cock the device and thus cannot attempt any "mock injection."

Further details and advantageous refinements of the invention will be apparent from the following description and drawings of an embodiment, which is not to be interpreted as any limitation of the invention.

BRIEF FIGURE DESCRIPTION

DETAILED DESCRIPTION

Figure 1:
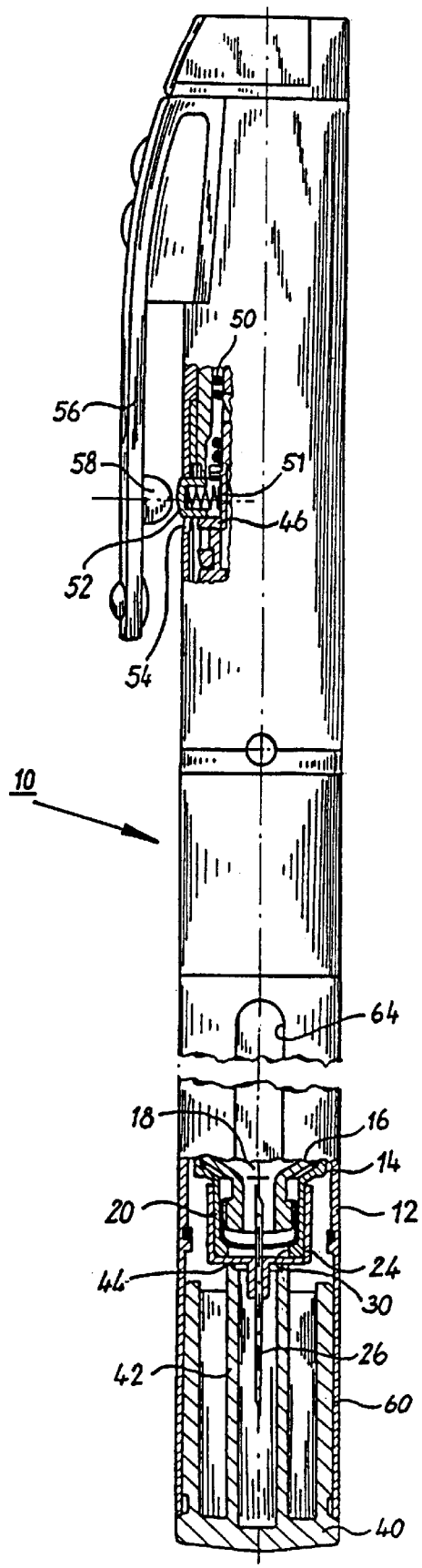
FIG. 1 is a side view of an injection device according to the invention, in which only certain parts are shown in longitudinal section.

FIG. 1 is a side view of an injection device 10.

According to standard medical terminology, in the following, the expressions "proximal" and "distal" are used, meaning: proximal=side adjacent the patient, thus in FIG. 1 the lower end with the injection needle 26; distal=side remote from the patient, thus in FIG. 1 the upper end.

Injection device 10 has a cylindrical housing 12, whose lower end is shown in FIG. 1 in section. In it, a cartridge holder 14 is arranged in a longitudinally movable manner. Inside it, there is a cartridge 16 with an injectable fluid 18.

The cartridge holder 14 transitions below into a neck 20 formed with an external thread 22, onto which the carrier 24 of a conventional injection needle can be screwed; see FIGS. 1 & 2.

Neck 20 at bottom has an axial opening 30, through which a distal portion 32 of the injection needle 26 extends, in order to pierce a rubber membrane 36 on the proximal end of cartridge 16, as is familiar to those in the art.

Figure 2:
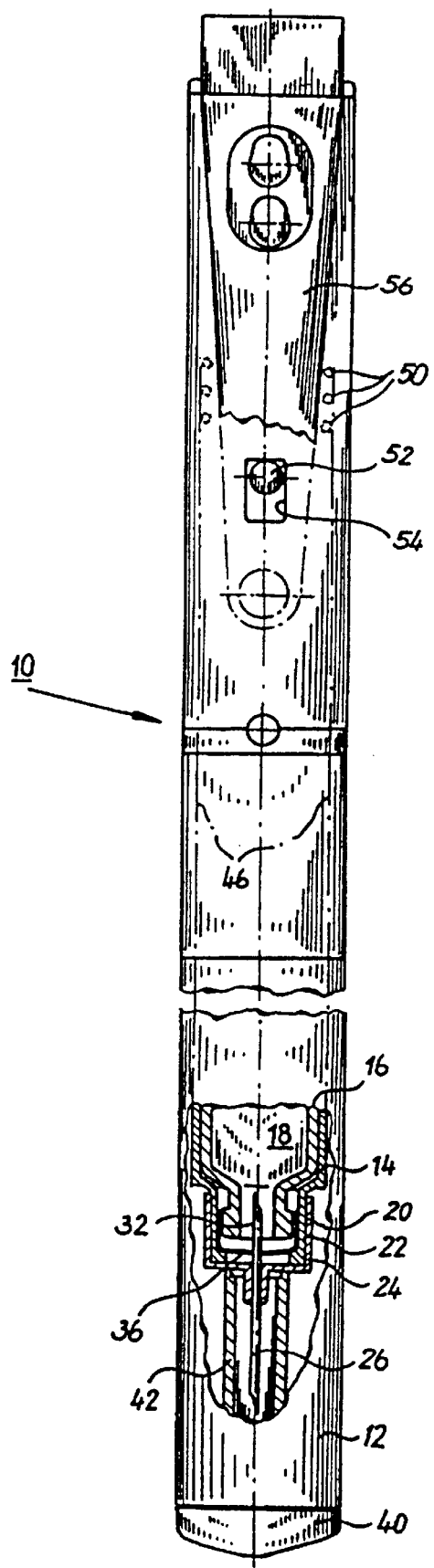
FIG. 2 is a view analogous to FIG. 1, but rotated 90° relative to FIG. 1.

When a needle 26 is mounted, its carrier 24 covers opening 30; see FIGS. 1 & 2. When, for cocking the injection device, a cocking member 40 is inserted into the proximal end of housing 12, as shown particularly clearly in FIG. 1, a central hollow-cylindrical portion 42 of cocking member 40 engages with its distal end 44 against carrier 24, and displaces it and the cartridge holder 14 in the distal direction.

As suggested in FIG. 2 by the dot-dashed lines 46, the cartridge holder 14 extends in the distal direction and transitions in its distal region into a setting mechanism (not shown) which is subjected to the force of an injection spring 50, shown only schematically in FIG. 2. FIG. 1 shows this spring in its compressed or cocked state.

The setting mechanism 46 has, in its distal region, a detent button 52 biased by a spring 51. Button 52 can latch into a detent opening 54 of housing 12, in order to latch the injection spring 50 in its biased configuration.

At the distal end region of housing 12, a clip 56 is attached. It is formed with a projection 58 which, when actuated, presses on the detent button 52 and thereby triggers an injection, as is known to those in the art.

Figure 3:
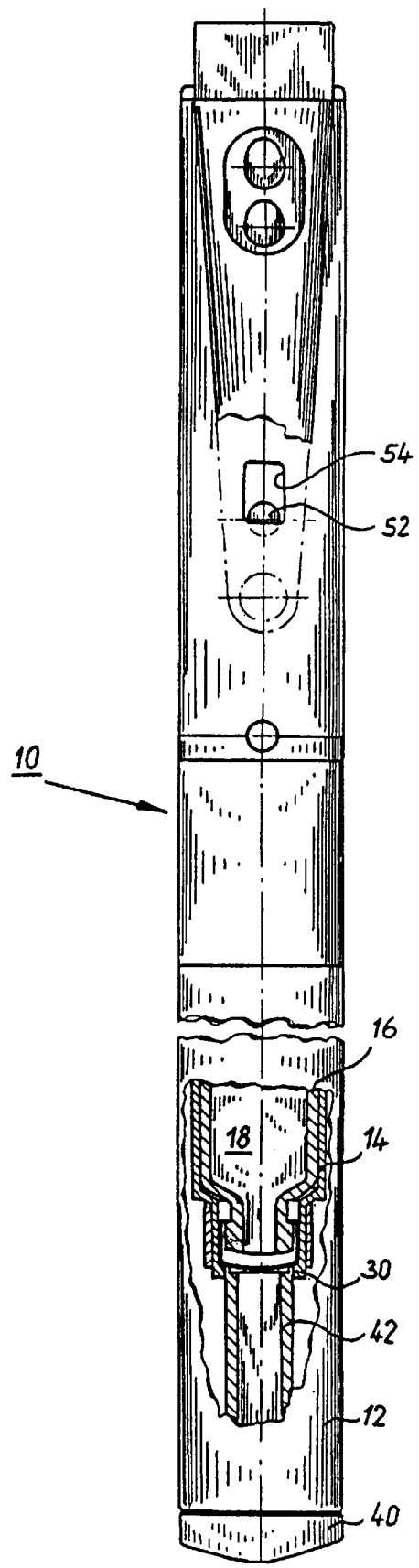
FIG. 3 is a view of the injection device of FIG. 2, in which however the patient has forgotten to mount a new injection needle, as a result of which the injection device cannot be cocked.

If the patient has forgotten to attach a needle 26, there results the situation of FIG. 3: the hollow cylindrical portion 42 of cocking member 40 extends through the axial opening 30 of cartridge holder 14 and comes into engagement against the proximal end of cartridge 16. Thereby, the setting mechanism 46 (FIG. 2) is displaced less far in the distal direction, so that, as shown in FIG. 3, detent button 52 cannot latch into detent opening 54, i.e. the injection device 10 cannot in this case be latched into its cocked configuration, and an injection is not possible.

Cocking member 40 can be formed with an external thread 60 (FIG. 1) which the patient can screw into a corresponding internal thread of housing 12, in order to cock injection device 46. In the cocked state according to FIG. 1 and 2, extension 42 of cocking member 40 covers needle 26 and protects it, and the device itself, from contamination. Prior to an injection, cocking member 40 is unscrewed or otherwise removed.

In the proximal portion of housing 12, a viewing window 64 (FIG. 1) is provided, in order to be able to see the state of fullness of cartridge 16.

Naturally, within the scope of the present invention, many variations and modifications are possible.

What is claimed is:

1. An injection device for use with a needle carrier supporting an injection needle, the device comprising:

a housing having a proximal end and a distal end;

an injection mechanism movable, relative to said housing, between an uncocked configuration and a cocked configuration, and a cocking device adapted to be applied at the proximal end of the housing to place said injection mechanism in said cocked configuration;

wherein placement into said cocked configuration is enabled, when a needle carrier has been inserted in said injection mechanism, and is disabled when a needle carrier is missing from said injection mechanism.

* * * * *

UNITED STATES PATENT AND TRADEMARK OFFICE
CERTIFICATE OF CORRECTION

| | |
|---|---|
| PATENT NO. | : 6,641,560 B1 |
| APPLICATION NO. | : 09/857717 |
| DATED | : November 4, 2003 |
| INVENTOR(S) | : Herbert Bechtold and Jochen Gabriel |

It is certified that error appears in the above-identified patent and that said Letters Patent is hereby corrected as shown below:

In column 4, after line 8, please insert the following Claims 2, 3, & 4:

2. An injection device for use with a needle carrier supporting an injection needle, the device comprising:

a housing having a proximal end and a distal end;

a container, movable relative to said housing between an uncocked position and a cocked position, and having a proximal end portion and a distal end portion, said container being adapted for receiving a cartridge of injectable fluid;

said container being adapted, at its proximal end portion, for releasable coupling of the needle carrier;

a spring provided in said housing for storing energy therein and for moving said container and said injection needle, relative to said housing, in a proximal direction by release of such energy;

a releasable detent latchable, relative to said housing, in a latching position wherein said spring stores energy;

a cocking device adapted to be applied at the proximal end of the housing for causing a cocking movement of the container in a direction toward the distal end of the housing, for storing energy in said spring concurrently with said cocking movement, and for moving said releasable detent toward said latching position, and wherein

UNITED STATES PATENT AND TRADEMARK OFFICE
CERTIFICATE OF CORRECTION

PATENT NO. : 6,641,560 B1
APPLICATION NO. : 09/857717
DATED : November 4, 2003
INVENTOR(S) : Herbert Bechtold and Jochen Gabriel It is certified that error appears in the above-identified patent and that said Letters Patent is hereby corrected as shown below:

In column 4, after line 8, please insert the following Claims 2, 3, & 4: (cont'd).

said cocking device has an element which, when the needle carrier is coupled to the proximal end portion of the container, engages the needle carrier, thereby controlling displacement of the container toward said cocked position, and wherein the releasable detent is movable into said latching position by said cocking member only when a needle carrier is coupled to the proximal end portion of the container.

3. The injection device according to claim 2, wherein the cocking member is shaped to surround, and thereby to protect from contamination, the needle, when present.

4. The injection device according to claim 2, wherein the cocking member is releasably received in the proximal end of said housing when inserted up to a predetermined end position.

Signed and Sealed this

Twelfth Day of June, 2007

JON W. DUDAS
*Director of the United States Patent and Trademark Office*